(12) United States Patent
Tumer et al.

(10) Patent No.: US 6,821,781 B1
(45) Date of Patent: Nov. 23, 2004

(54) METHOD FOR SELECTING TRANSFORMED PLANT CELLS USING ETHIONINE AND CYSTATHIONINE GAMMA SYNTHASE AS THE SELECTION AGENT AND MARKER GENE

(75) Inventors: Nilgun E. Tumer, Belle Mead, NJ (US); Thomas Leustek, Union, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 0 days.

(21) Appl. No.: 09/936,454

(22) PCT Filed: Mar. 20, 2000

(86) PCT No.: PCT/US00/07330

§ 371 (c)(1),
(2), (4) Date: Sep. 13, 2001

(87) PCT Pub. No.: WO00/55303

PCT Pub. Date: Sep. 21, 2000

Related U.S. Application Data

(60) Provisional application No. 60/125,654, filed on Mar. 22, 1999, and provisional application No. 60/124,961, filed on Mar. 18, 1999.

(51) Int. Cl.[7] .......................... C12N 5/04; C12N 15/82; A01H 1/04; A01H 5/00
(52) U.S. Cl. ........................ 435/419; 435/468; 435/417
(58) Field of Search ................................ 435/419, 468, 435/417, 320.1; 800/278, 298

(56) References Cited

U.S. PATENT DOCUMENTS

| | | | |
|---|---|---|---|
| 5,589,616 A | 12/1996 | Hoffman | 800/205 |
| 5,633,436 A | 5/1997 | Wandelt | 800/205 |
| 5,902,616 A | 5/1999 | Hinnergardt et al. | 426/52 |
| 5,912,414 A * | 6/1999 | Falco et al. | 800/205 |
| 5,928,701 A | 7/1999 | Jensen et al. | 426/560 |
| 5,952,026 A | 9/1999 | Greenway et al. | 426/241 |
| 5,965,189 A | 10/1999 | Stevens et al. | 426/549 |
| 5,965,190 A | 10/1999 | Gallaher et al. | 426/615 |
| 5,968,585 A | 10/1999 | Liaw et al. | 426/656 |
| 6,004,591 A | 12/1999 | Hinnergardt et al. | 426/52 |

FOREIGN PATENT DOCUMENTS

| | | |
|---|---|---|
| WO | 95/31554 | 11/1995 |
| WO | 98/55601 | 12/1998 |

OTHER PUBLICATIONS

Inaba et al. Isolation of *Arabidopsis thaliana* mutant mto1, that overacumulates soluble methionine. Plant Physiology, 1994, Vo 104, pp. 881–887.*

Brinch–Pedersen et al. Engineering of the aspartate family biosynthetic pathway in barley by transformation with heterologous genes encoding feed–back–insensitive aspartate kinase and dihydrodipicolinate synthase. Plant Mol. Biol. 1996; 32(4):611–620.*
Kim et al., Plant Molecular Biology, 32: 1117–1124 (1996).
Ravanel et al., Archives of Biochemistry and Biophysics, vol. 316, No. 1, pp. 572–584 (Jan. 10, 1995).
Boerjan et al., The Plant Cell, vol. 6, No. 10, pp. 1401–1414 (Oct. 1994).
H.V. Davis, Potato Research, vol. 39, pp. 411–427 (1996).
Gert Ooms, Journal of The Science of Food and Agriculture, vol. 54, pp. 157–163 (1991).
Fierabracci et al., Journal of Chromatography, vol. 570, pp. 285–291 (1991).
Inaba et al., Plant Physiology, vol. 104, No. 3, pp. 881–887 (Mar. 1994).
Tu, et al., "Expresssion of the Brazil Nut Methionine–Rich Protein in Transgenic Potato Plants". In: The Molecular and Cellular Biology of the Potato, Second Edition, Edited by Belknap, et al. Wallingford: CAB International, 1994, Chapter 15, pp. 209–220.
Altenbach, et al. "Enhancement of the Methionine Content of Seed Proteins by the Expression of a a Chimeric Gene Encoding a Methionine–rich Protein in Transgenic Plants", In: Plant Molecular Biology, 1989, vol. 13, pp. 513–522.
Curien, et al. "Characterization of an *Arabidopsis thaliana* cDNA encoding an S–adenosylmethionine–sensitive threonine synthase. Threonine Synthase from Higher Plants". FEBS Letters, 1996, vol. 390, pp. 85–90.
Hughes, et al. "Identification and Expression of a cDNA Encoding Cystathionine Gamma–Synthase in Soybean". In: Plant Science, 1999, vol. 146, pp. 69–79.

* cited by examiner

*Primary Examiner*—Amy J. Nelson
*Assistant Examiner*—Cynthia Collins
(74) *Attorney, Agent, or Firm*—Lerner, David, Littenberg, Krumholz & Mentlik, LLP

(57) ABSTRACT

Disclosed are transgenic plants having edible portions that produce methional during processing. The plants contain increased methionine levels such that upon processing of the edible portion(s), methional levels are increased and lead to food products that possess improved flavor stability and/or quality. Plants of the Solanaceous family e.g., potato, tomato and eggplant, and other methional-producing plants including maize and soybean, are preferred plants. Several ways of genetically engineering plants to produce increased free Met levels are disclosed, with introduction of a non-native nucleic acid encoding cystathionine gamma synthase (CGS) and tissue-specific expression of an anti-sense S-adenosylmethionine synthetase being preferred. Also disclosed are methods for selecting transformed plant cells using ethionine and CGS as the selection agent and marker gene respectively.

8 Claims, 3 Drawing Sheets

METHOD FOR SELECTING TRANSFORMED PLANT CELLS USING ETHIONINE AND CYSTATHIONINE GAMMA SYNTHASE AS THE SELECTION AGENT AND MARKER GENE

PRIORITY INFORMATION

This application is a §371 national phase entry of PCT/US 00/07330, filed Mar. 20, 2000, which claims benefit under §119(e) on the basis of U.S. Provisional Patent Application Nos. 60/125,654, filed Mar. 22, 1999, and 60/124,961, filed Mar. 18, 1999.

TECHNICAL FIELD

The present invention relates generally to the field of agricultural biotechnology and more particularly to transgenic plants exhibiting enhanced flavor quality and stability, and methods of making the plants.

BACKGROUND ART

Methionine (Met) is the precursor for methional, an important flavor compound in various plants such as potatoes, as well as in meats and cheese cracker flavors. The production of methional is thermally induced. It is formed as a result of the interaction of alpha-dicarbonyl compounds, which are formed during the Maillard reaction, with Met through the Strecker degradation reaction. Methional readily decomposes to yield methanethiol, which oxidizes to dimethyl disulfide. Furthermore, derivatives of methionine, such as S-methylmethionine, release dimethyl sulfide that is responsible for the aromas of fish, canned sweet corn, tomato juice and stewing oysters and clams. Methional and S-methyl methionine are heat labile and readily decompose during food processing. Due to high costs of production, these flavor compounds as well as the Met precursor are not added back during food processing.

Met, a sulfur containing amino acid is extremely important in all living organisms. Met serves central roles in metabolism as the initiator tRNA in protein synthesis, as S-adenosylmethionine (SAM), the primary methyl donor for most transmethylation reactions and as a precursor for polyamines and the phytohormone, ethylene in plants. Animals cannot synthesize Met, for this reason it is considered an essential amino acid for animal nutrition.

Due to the nutritional importance of Met, there have been attempts to develop plants with high Met content by genetic engineering. It has been discovered that an abundant seed protein in Brazil Nut (BNP) contains an exceptionally high content of Met (18%) and Cys (8%) (Ampe, et al., Eur. J. Biochem. 159:597–604 (1986); Sun, et al., Eur. J. Biochem 162:477–483 (1987)). Heterologous over-expression of BNP in transgenic tobacco (Altenbach, et al., Plant Mol. Biol. 13:513–522 (1989)) and Brassica (Guercbe, et al., Mol. Gen. Genet. 221:306–314 (1990) ) resulted in a 30% increase in seed Met content. Transgenic plants over-expressing a Met-rich protein such as a sunflower seed albumin (Molvig, et al., Proc. Natl. Acad. Sci USA 94:8393–8398 (1997)) also showed a 94% increase in Met content. An unfortunate property of BNP is that it is a potent allergen in humans with allergies to nuts making the transgenic plants unsuitable for human consumption. See Nordlee, et al., N. Eng. J. Med. 334:688–692 (1996) and Bartolome et al., Allergol. Immunopathol. (Madrid) 25:135–144 (1997). These high-Met proteins are not metabolized to release free Met, however, until consumption. Thus, there is no increase in free Met levels prior to processing and no increase to in methional levels during processing.

Other attempts have focused on deregulation of the Asp family pathway. Transgenic tobacco seeds over-expressing bacterial feedback insensitive aspartate kinase showed a 15.5-fold increase in Thr content but only a 3-fold increase in Met (Shaul, et al., Plant Mol. Biol. 23(4):759–768 (1993); Karchi, et al., Proc. Natl. Acad. Sci. USA 91:2577–2581 (1994). This suggests that the carbon skeleton is not limiting for Met synthesis and that a Met-specific regulation exists. It was also revealed that there was no direct correlation between Lys level and the dihydrodipicolinate synthase (DHPS) activity in transgenic plants over-expressing the feedback-insensitive bacterial DHPS (Ben-Tzvi Tzchori, et al., Plant Mol. Biol. 32:727–734 (1996). The free Lys level was significantly reduced in mature seeds because Lys is efficiently catabolized (Karchi, et al., supra). Further analysis revealed that a Lys degradation pathway was induced in the transgenic plants (Galili, et al., Plant Cell 7:899–906 (1995)). Another attempt to overproduce Met in Arabidopsis was to select for mutants resistant to ethionine, a toxic analog of Met (Alix, Microbiol. Rev. 46(3):281–295 (1982)). Mutants that are resistant to ethionine have been characterized in cultured plant cell lines (Widholm, Can. J. Bot. 54:1523–1529 (1976); Reish, et al., Theor. Appl. Genet. 59:89–94 (1981); Gonzales, et al., Plant Physiol. 74:640–644 (1984); *Madison and Thompson*, Plant Cell Rep. 7:473–476 (1988)) all of which are reported to accumulate Met. One *Arabidopsis* mutant termed the mtol showed over-accumulation of soluble Met at the vegetative growth stage but the Met level returned to normal after flowering (Inaba, et al., Plant Physiol. 104:881–887 (1994)).

Hence, a need remains for reliable methods for preparing transgenic plants having increased free met content, and particularly plants that are processed into foodstuffs and food additives.

SUMMARY OF THE INVENTION

One aspect of the present invention is directed to transgenic plants of the Solanaceous family e.g., tomato, potato and eggplant, containing at least one non-native nucleic acid that when expressed in the plants, results in increased free methionine levels relative to native free methionine levels. Processing of edible portions of the plant e.g., to make a food product or food additive containing the processed plant portion(s), results in an increase in methional levels compared to methional levels present in a processed edible portion of a wild-type plant. In preferred embodiments, the non-native nucleic acid encodes cystathionine gamma synthase (CGS). In other preferred embodiments, increased free methionine levels in potatoes result from expression of a nucleic acid containing a tuber-specific promoter regulatory unit operably linked (in operative association with) and anti-sense S-adenosyl-methionine synthetase (SAMS)-encoding nucleic acid. In yet other preferred embodiments, a non-native nucleic acid containing a tuber-specific promoter linked to a DNA molecule encoding a SAMS DNA in the sense orientation, that is homologous to the potato. Seed derived from the transgenic plants are also provided.

Another aspect of the present invention is directed to transgenic plants having edible portion(s) that produce methional when processed, such as maize and soybean plant, that contain increased free methionine levels relative to native free methionine levels. Maize is especially preferred. Edible portions of these plants contain increased methional levels compared to methional levels in a processed, wild-type plant. The increased free methionine levels are achieved by expression of a non-native nucleic acid that is other than a nucleic acid encoding a plant CGS, particularly in the seeds of the plants.

Yet another aspect of the present invention is directed to methods of making the aforesaid transgenic plants.

A further aspect of the present invention is directed to making processed products such as foods or food additives containing edible parts thereof that exhibit increased flavor stability and/or quality. The methods entail preparing the aforesaid transgenic plants that contain increased methionine levels, and harvesting and then processing the plant parts, whereupon the processing results in increased methional levels. Products such as foods and food additives that contain the processed plant or parts thereof are also provided.

Yet a further aspect of the present invention is directed to a method for selecting plant cells containing a non-native nucleic acid of interest (e.g., a structural gene encoding a protein of interest), and a selection agent/marker gene combination for use therewith. The method entails transforming plant cells with a chimeric nucleic acid that contains inoperable association, a promoter functional in a plant cell and a first and a second DNA molecule. The first DNA molecule is preferably a structural gene encoding a protein of interest and the second DNA molecule encodes a CGS that permits the selection of a transformed plant cell containing the chimeric nucleic acid molecule by rendering the transformed plant cell resistant to an amount of ethionine that would be toxic to a plant cell that does not express the DNA encoding the CGS. The transformed plant cells are cultured in medium containing ethionine in an amount that would be toxic to plant cells that do not express the CGS-encoding DNA. Plant is cells that grow in the medium are selected. The chimeric nucleic acids, plant cells transformed a therewith, and compositions of matter containing the transformed plant cells in medium containing ethionine are also provided.

BRIEF DESCRIPTIONS OF THE DRAWINGS

FIG. 1 is a flow diagram showing the biosynthetic pathway of methionine in plants, wherein ACC means 1-aminocyclopropane-1-carboxylic acid, CGS means cystathionine gamma-synthase, DMS means dimethylsulfide, SMSP means dimethylsulfoniopropionate, Hcy means homocysteine, Kan® means kanamycin resistant, MTA means 5-methylthioadenosine, MTHB means 4-methylthio-2-hydroxy butryic acid, MTOB means 4-methylthio-2-oxobutanoic acid, OPH means O-phosphohomoserine, PITC means phenylisothiocyanate, SAH means S-adenosyl-L-homoserine, SAM means S-adenosyl-L-methionine, SAT means serine acetyltransferase, SMM means S-methylmethionine and TS means threonine synthase.

DETAILED DESCRIPTION OF THE PREFERRED EMBODIMENTS

Figure 1:
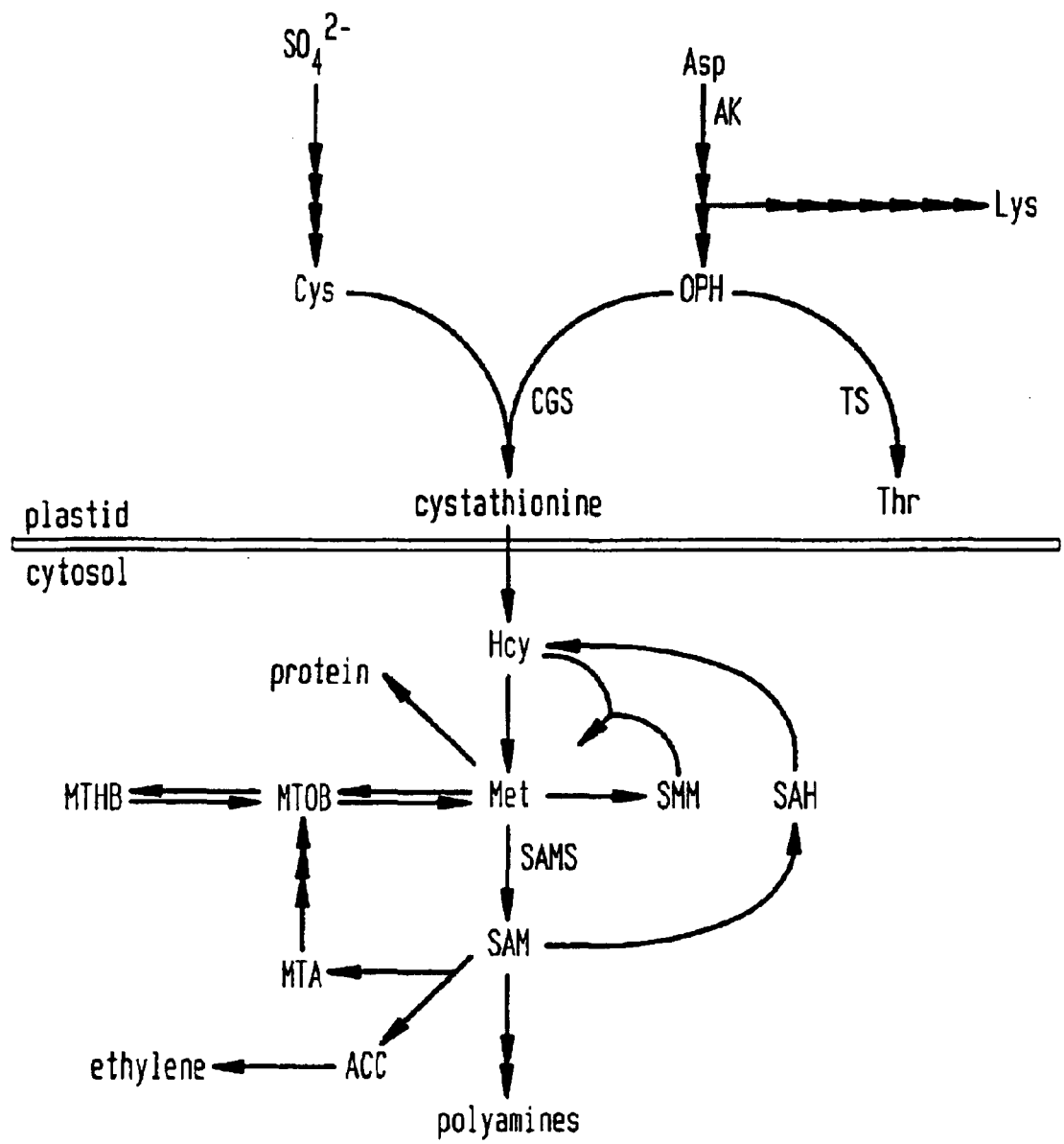

Met, along with threonine (Thr), lysine (Lys) and isoleucine (Ile) are derived from aspartic acid (Asp). The pathway for Met synthesis varies among different organisms. The first step in the pathway is the phosphorylation of Asp by the enzyme aspartokinase to generate O-phospho-L-homoserine (OPH). In plants, the first enzyme committed to Met biosynthesis, cystathionine-γ-synthase (CGS), catalyzes the condensation of O-phospho-L-homoserine (OPH) and cysteine (Cys) to form cystathionine. The second enzyme in the pathway, cystathionine-β-lyase, cleaves cystathionine to form L-homocysteine and L-serine. Met is then formed by transmethylation of L-homocysteine. The enzymes involved in the Met biosynthetic pathway are distributed between plastids and cytosol. CGS is localized exclusively in the chloroplasts.

Free Met levels are increased (relative to wild-type or non-transformed plant) by over-expressing or inhibiting expression of enzymes involved in its biosynthetic pathway. The present invention is particularly suited to members of the Solanaceous family, e.g., potato, tomato and eggplant, as well as to other plants that produce methional when processed, such as maize and soybean . For example, over-expression of CGS or the inhibition of S-adenosyl-methionine synthetase (SAMS) or threonine synthase, will increase free Met levels.

In preferred embodiments, a transgenic plant is prepared that over-expresses CGS. DNAs encoding this enzyme have been isolated and sequenced from a variety of plant species including ice plant, potato, maize (WO/9531554), soybean, spinach (Ravanel, et al., Arch. Biochem. Biophys. 316:572–584 (1995)) and tobacco (Steegborn, et al., J. Mol. Biol. 290(5):983–996 (1999) and *Arabidopsis* (Kim, et al., Plant Mol. Biology 32:1117–1124 (1996)), as well as yeast, bacteria and algae. CGS genes from other plant species can be identified by constructing a plant cDNA library in an *E. coli* mutant that bears a metB mutation and thus does not grow in the absence of methionine. Expression of the plant CGS gene allows the bacterial stain to grow in the absence of methionine. See, In WO/95/1554 and Kim, et al., supra. Other plant CGS genes showing high sequence similarity to the wild-type *Arabidopsis* CGS gene have been cloned from *Zea mays* (AF007785, AF007786), *Fragaria vesca* (AJ001451, Nam, et al., Plant Mol. Biol. 39:629–636 (1999)), *Mesembryanthemum crystallinum* (AF069317), *Solanum tuberosum* 9AF1441025, AF082891, AF082892), *Glycine max* (AF141602, Hughes, et al., Plant Sci. (In press (1999)) and *Nicotiana tabacum* (AF097180). The potato CGS genes show 93% sequence similarity as well as high sequence similarity with other plant CGS genes, including *Arabidopsis*. The N-terminal region of the potato CGS genes contain typical features of transit peptides for localization to plastids and the conserved region of MTO1 which has been shown to regulate CGS expression in *Arabidopsis*. See, Chiba, et al., Science 286:1371–1373 (1999).

Mutant forms of CGS are also useful. Chiba describes five different CGS alleles in *Arabidopsis* (i.e., Mtol-1, Mtol-2, Mtol-3, Mtol-4 and Mtol-5) resulting from point mutations that were found to be concentrated in a region of exon1 of the CGS gene termed MTO1. This region consists of approximately 30 amino acids that are highly conserved among plant CGS sequences. Application of exogenous free Met to wild-type plants results in a decrease in CGS mRNA. The deduction, therefore, is that CGS normally regulates its own synthesis in plants. That is, mRNA synthesis decreases with increasing levels of free Met. The mtol mutants described in Chiba over-accumulate free Met, indicating CGS mRNA levels were not down-regulated in the presence of free Met. The mutations give rise to amino acid substitutions near the N-terminus of each of the 5 encoded CGS proteins, namely Gly84Ser, Ser81Asn, Gly84Asp, Arg77His and Gly84Asp respectively. These mutations can be introduced into the wild-type *Arabidopsis* CGS gene using site-directed mutagenesis, thus producing DNAs encoding mutant, non-self regulating CGS.

Inhibition of SAMS is another preferred approach to increase Met levels in potato. SAMS catalyzes the synthesis of S-adenosyl methionine (SAM), a common methyl donor in various methylation reactions, from Met and ATP. This reaction consumes two high energy phosphate bonds of ATP releasing pyrophosphate. Thus, Met is a substrate of SAMS and SAMS activity results in a decrease in free Met levels. The enzymatic and structural properties of SAMS have been well studied in *E. coli*. The SAMS from *E. coli* is a homotetramer consisted on four 383-residue monomer (Markham, et al., J. Biol. Chem. 255:9082–9092 (1980)) and it requires $Mg^{2+}$ and $K^+$ for maximal activity. Plant SAMS sequences have been reported from various plant species. In all cases examined, SAMS was found to be encoded by small gene family. There are 2 genes found in *Arabidopsis* (Peleman, et al., Plant Cell 1:81–93 (1989), 4 genes in tomato (Espartero, et al., Plant Mol. Biol. 25(2):217–227 (1994)), and 3 genes in *Catharanthus roseus* (Schröder et al., Plant Mol. Biol. 33:211–222 (1997)). In the case of SAMS, Applicants believe (while not intending to be bound by any particular theory of operation) that the effect may result from blocking a major route for methionine metabolism and increasing the rate of methionine synthesis. SAMS is encoded by a gene family present in most angiosperms. One gene is expressed in vascular tissue of roots, stems and leaf, and the other is expressed in mesophyl cells of roots stems and leaf. The SAMS expressed in vascular tissue may function in supplying S-adenosylmethionine, the primary methyl group donor, for lignin biosynthesis in vascular cells with extensive secondary cell wall synthesis. Both forms encode cytosolic enzymes. The form expressed in mesophyll cells may provide S-adenosylmethionine for other metabolic reactions including polyamine biosynthesis and others.

Complete inhibition of SAMS in tobacco and *Arabidopsis* was achieved through co-suppression (Boerjan, et al., Plant Cell 6:1401–1414 (1994)). Co-suppression centers on overexpression of a specific gene with the effect that both the transgene and endogenous gene (or genes in a family) are silenced. The effect is usually complete inhibition of an enzyme, as is the case with SAMS. General and complete inhibition of SAMS in all plant tissues, as described in Boerjan, however, is accompanied by severe growth stunting and other growth abnormalities. Thus, the present invention entails the partial inhibition in this enzyme in specific tissues, namely tubers, to achieve the accumulation of methionine without affecting growth or development of the plant. More specifically, increasing the methionine content of potato may be achieved through repression of SAMS specifically in tubers, optionally in combination with expression of trans-CGS as described above.

In one embodiment, SAMS expression is partially repressed using antisense DNA. This technology involves expression of a transgene, cloned in reverse (or anti-sense) orientation relative to a promoter sequence for regulating transcription of the DNA. The anti-sense transcript is believed to hybridize to the endogenous sense transcript, blocking its translation and targeting it for degradation. The important features of this technology are that only transcripts with significant nucleotide sequence similarity to the anti-sense are targeted for repression, and the repression is usually incomplete. Depending upon the specific transgenic isolate, the effect of the anti-sense ranges from nearly complete repression to slight repression. In so doing, specific SAMS isoenzymes may be repressed, specifically in potato tubers. Thus, in the present invention, an SAMS anti-sense nucleic acid is operably linked to a tuber specific promoter. A preferred promoter is the patatin promoter. Other such promoters, in their native state, regulate transcription of mRNA encoding proteins involved in starch biosynthesis that occurs in tubers.

In another embodiment, partial suppression of SAMS in tubers is achieved via co-suppression wherein a SAMS-encoding nucleic acid is operably linked to a potato tuber specific promoter. Here, the trans-nucleic acid is preferably homologous to the plant and embraces tuber-specific overexpression of the native SAMS gene. Thus, by the term "non-native", it is meant different from the native genome or in addition to the native genome of the plant.

Other methods of increasing Met content entail a total bypass of the Met biosynthetic pathway by expression of a transgene such as bacterial CGS that directs the direct sulfhydration of homoserine. Bacterial CGS genes may also be used in the present invention. Bacterial CGS has been well studied and is known to use 0-succinylhomoserine (OSH) or 0-acetylhomoserine (OAH), depending on the species, as the physiological substrate. The bacterial enzyme catalyzes a γ-elimination reaction in the absence of Cys to yield succinate, α-ketobutyrate and ammonia. The nucleic acid sequence and these various properties of bacterial CGS are reported in Holbrook et al., Biochem. 16:435442 (1990).

Another method involves co-expression of a methionine-rich protein and a protease in different cellular compartments. Upon potato processing, the protease is allowed to come into contact with the Met-rich protein, cleaving it into free Met residues. Yet another method entails expressing an anti-sense DNA encoding threonine synthase (TS) or DNAs encoding mutant TSs that inhibit or reduce the amount of TS synthesized by the plant cell. Free Met levels increase when TS is inhibited or reduced.

The present invention is also applicable to plants other than members of the Solanaceous family that produce methional when processed. These plants include maize and soybean plants. Applicants have discovered that processed edible parts of such transgenic plants having relatively high free Met levels compared to wild type plants have significantly improved flavor stability and/or quality and nutritional quality relative to processed parts obtained from plants containing native methional levels. Transgenic plants are prepared preferably using techniques described above other than a plant CGS-encoding transgene and less preferably, any CGS gene. In the case of soybeans and maize, the non-native nucleic acid e.g., the anti-sense SAMS, is preferably expressed in the seeds, which is the edible part of these plants that is processed. Methods and regulatory sequences useful for seed-specific expression of trans-nucleic acid in seed-containing plants are described and/or referenced in WO 9531554.

Genetic constructs and other reagents, as well as techniques for genetic manipulation of Solanaceous plants and other plants such as maize and soybean are known in the art. See, e.g., Davies, "Recent Developments in Our Knowledge of Potato Transgenic Biology," Potato Res. 39(Extra Ed.): 411–427 (1996) (and references cited therein); Belknap, et al. (eds.), *The Molecular and Cellular Biology of the Potato*, $2^{nd}$ Ed., CAB International (Wallingford), 1994 (and references cited therein); J. Sci. Food and Agri. 54(1):157–163 (1991) (describing, inter alia, vectors and transformation systems for potato); Vayda, et al, Trans. Res. 1(4):149–163

(1992) and WO 9531554 and Newell, et al., Plant Cell Rep. 10:30–34 (1991). A preferred method for dicots entails indirect gene transfer with *Agrobacterium tumefaciens*-mediated transformation of potato tissue, and regeneration of the transformed tissue into whole plants. Preferred methods of direct gene transfer into monocots include PEG-mediated gene transfer and particle bombardment. Seed may be derived from the plants in accordance with standard methods.

Processing of the plant such as potato results in increased levels of methional relative to plants having native or wild type levels of free Met, which in turn results in increased flavor and nutritional quality. The term processing is meant to include cooking, dehydrating, baking and other activities that are performed to prepare various plant products and/or parts thereof for human consumption. In the case of potato, the edible portion is the tuber and such products include frozen (freeze dried) potato products, boiled or baked potato, mashed potato, escalloped potato, potato chips and types of fried potato (e.g., french fries). In the case of tomatoes, the edible portion is the fruit and such products include processed tomatoes, canned tomato products such as pastes, sauces, juices, and the like. Processed corn products include corn fries, canned corn etc. Literature directed to methods for making food products using plants and plant parts is legion. See, e.g., U.S. Pat. Nos. 5,952,026 and 5,965,591 (processed potato products), U.S. Pat. Nos. 5,902,616, 6,004,591 and 5,965,190 (processed tomato products) and U.S. Pat. Nos. 5,968,585 and 5,928,701 (processed corn products).

Another aspect of the present invention is directed to a marker gene/selection agent combination that is used to identify cells transformed with a nucleic acid of interest. Ethionine is an analog of Met that is very toxic to plants. Applicants have discovered that plants that over-produce CGS are resistant to CGS. Accordingly, this aspect of the present invention entails use of the CGS/ethionine selection system for plant cells much in the same way that popular selection systems e.g., neomycin/NPTII and BASTA/Bargene, are used. The CGS DNA is incorporated into an expression cassette that also includes the nucleic acid of interest. In preferred embodiments, a nucleic acid encodes a protein e.g., a protein that confers a phenotypic change to the plant. Following transformation, cells are cultured on medium containing ethionine. The amount of methionine added to the medium varies depending upon the type of plant cells being cultured, and may be determined by persons skilled in the art in accordance with standard techniques. In Example 1 below, concentrations of ethionine ranging from 10–300 $\mu$M were added to cultures of transformed potato cells. Cells/protoplasts that grow in the presence of ethionine are selected. The advantage of the presently disclosed selection system is that because CGS is a plant enzyme, its use as a selectable marker would preclude the regulatory issues associated with the use of antibiotic resistance markers, such as the bacterial neomycin phosphotransferase (NPTII) gene commonly used in transgenic plants. The present method is applicable to any plant cell, including both monocots and dicots. Typically, monocots are transformed using particle bombardment or via PEG-mediated uptake, and dicots are transformed using *Agrobacterium tumafaciens*-mediated gene transfer.

The products and methods of the present invention are further illustrated by the following examples. The presentation of these examples is by no way intended to limit applicants' invention in any way. Unless otherwise specified, all percentages are by weight.

EXAMPLES

Example 1

Constitutive Expression of *Arabidopsis* CGS in Potato

The following example describes the isolation of a cDNA clone encoding CGS from *Arabidopsis thaliana* complementation of a CGS mutant strain of *E. coli* (met B) (Kim, et al., (1996). CGS is a single copy gene in *Arabidopsis*. The coding sequence is 1692 bp and encodes a 563 amino acid protein. To increase free methionine levels in potato tubers, the cDNA encoding the *Arabidopsis* CGS was expressed in Russet Burbank potato. The transgenic potato plants were analyzed for expression of CGS, CGS activity, and free methionine levels.

Preparation of the CGS[+] Construct

A plant expression vector was prepared for overexpression of CGS in transgenic potato plants by subcloning the 2.0 kb KpnI-XbaI fragment from the full-length CGS cDNA (GenBank Accession number U43709; Kim, et al., Plant Mol. Bio. 32(6):1117–1124 (1996)) into the same sites of pFF19 as a transcriptional fusion with the CaMV 35S promoter. The entire expression cassette was subcloned as a 3.0 kb HindlII-EcoRI fragment into same sites of pBI101 (Clonetech) in the sense orientation CGS[+].

Transformation of Potato

The CGS[+] construct was used to transform *A. tumefaciens* stain pGV2260 by electroporation (BioRad, Inc., Gene Pulser™). Ten milliliters of overnight-grown *A. tumefaciens* was inoculated into 1 L of YEP medium (for 1 L, 10 g of Bacto-peptone, 10 g of Bacto-yeast extract, and 5 g of NaCl, pH 7.0) and the culture was grown to an OD600 of 0.4 at 30° C. The cells were harvested at 4° C. by centrifugation at 4000 g for 10 min. and resuspended in 1 L of ice cold water. The process was repeated once more. The cells were then washed twice in 50 ml of ice cold 10% (v/v) glycerol. Finally the cells were resuspended in 10 ml 10% (v/v) glycerol and stored at −70 C. This strain was transformed with the CGS[+] construct using a cuvette with 0.2 cm electrode gap at a setting of 25 mF, 200, and 2.5 kV. Transformants were selected on YEP medium with 1.5% (w/v) agar containing Kan (50 mg/ml) at 30° C. Transformants were confirmed to carry specific plasmids by Southern blotting. Russet Burbank potato was transformed using the *A. tumefaciens* strain pGV2260 carrying the CGS[+] construct using cultured potato stems as explants. 8–10 mm long stems were co-cultivated with *Agrobacterium* carrying CGS [+] resuspended in water. The stems were then placed on petri dishes containing MSO medium (MS, 3% sucrose and 1x vitamin) for two days in the dark. They were then transferred to PC medium (MS salts with 100 mg/l myo-inositol, 0.1 mg/l NAA, 3% sucrose, 5 mg/l AgNO3, 0.5 mg/l zeatin, 100 mg/l kanamycin for selection and 300 mg/l cefataxime to prevent contamination) for the induction of callus tissue. One month later, the tissues were placed on PS medium (MS, 100 mg/l inositol, 1x vitamin, 3% sucrose, 0.3 mg/l gibberellic acid, 5 mg/l zeatin, 100 mg/l kanamycin and 300 mg/l cefataxime) to induce shoots. In 4–8 weeks, the induced shoots were transferred to PM medium (MS, 3% sucrose, 170 mg/l NaH$_2$PO$_4$—H$_2$O, 0.4 mg/l thiamine, 100 mg/l myo-inositol and 1x vitamin) for the growth of roots. The plantlets were then transferred to soil and acclimatized to the greenhouse conditions.

Southern and Northern Blot Analysis

Genomic DNA was isolated from potato plants using a modified purification method. Plant tissues were ground in liquid nitrogen and resuspended in urea extraction buffer (2.8 M urea, 0.125 M NaCl, 20 mM Tris-HCl, pH 8.0, 8 mM EDTA, 0.4% sarkosyl (a detergent). After extraction with phenol/chloroform, genomic DNA was precipitated by isopropyl alcohol and resuspended in TE buffer. Total RNA was isolated using TRI REAGENT (T-9424, Sigma) according to the manufacturer.

Southern and Northern blot analyses were carried out as described by Sambrook, et al., *Molecular Cloning: A Laboratory Manual*, $2^{nd}$ Ed., Cold Spring Harbor: Cold Spring Harbor Laboratory Press (1989). After electropberesis, nucleic acids were transferred to Duralose-UV membranes (#420113, Stratagene) by capillary action. $^{32}$P-dCTP labeled probe was made with the full-length CDNA of *Arabidopsis* CGS using the READY-TO-GO DNA labeling beads (#27-9240-01, Amersham Pharmacia Biotech Inc.). Hybridizations were carried out at 68° C. overnight. After several washes, the membranes were exposed to Kodak X-OMAT film.

Immunoblot Analysis of CGS Expression

CGS protein levels were determined in transgenic potato plants by immunoblotting as previously described (Wang, et al., Plant Physiol. 102:843–850 (1993)). Soluble protein extracts were prepared from leaves, roots and tubers of transgenic potato plants by grinding the plant tissues in liquid nitrogen and resuspending the powder in 50 mM Tris-HCl, pH 8.0. The homogenate was centrifuged at 4° C. to remove cellular debris, and the final supernatant was used for immunoblot analysis. Protein concentrations were determined using the Bradford dye-binding assay with BSA as a standard (BioRad, Inc.). Protein samples (10 µg) were electrophoresed on an SDS-PAGE gel prepared with 10% (w/v) acrylamide and blotted onto Immobilon-P membrane (Millipore Corp.) at 4° C. for 1 hr. using transfer buffer containing 25 mM Tris, 250 mM glycine and 20% (v/v) methanol. The membrane was blocked with 1% (w/v) blocking reagent Boehringer Mannheim) overnight at 4° C. Antiserum against *Arabidopsis* CGS was used at a dilution of 1:2000 in PBST (0.1 M phosphate buffer pH 7.4, 15 mM NaCl, 3 mM KCl, 0.2% (v/v) Tween-20). The membrane was incubated with antibodies for 1 hr. and then the membrane was washed with PBST 3 times for a total washing time of 1 hr. The membrane was then incubated with a goat anti-rabbit IgG conjugated to horseradish peroxidase (Sigma, A0545) diluted 1:10000 in PBST buffer for 30 min. After washing with PBST 3 times for total of 30 min., the antibody complexes were detected with the Renaissance Kit (Dupont NEN, Inc.) and Kodak X-OMAT™ film (Eastman Kodak Com., NY).

CGS Enzyme Assay

Potato tissues were frozen in liquid nitrogen and then ground into a fine powder. The powder was resuspended in 20 mM Mops-NaOH, pH 7.4 and then centrifuged at 6000 g for 10 min. CGS activity in the supernatant was measured as described by Ravanel, et al., Arch. Biochem. Biophys. 316:572–584 (1995), using OSH as a substrate. Although plant CGS uses OPH as the physiological substrate, it can also use a variety of homoserine esters including OSH (Ravanel, (1995)) which is the only one that is commercially available. Enzyme activity was measured in a volume of 100 ml containing 20 mM Mops-NaOH, pH 7.4, 0.5 mM Cys, 10 mM OSH, 1 mM DTT and plant extracts. Assays were initiated by adding substrate. After incubation at 20° C. for 2 to 30 min., the reaction was stopped by addition of 50 ml 20% (w/v) TCA. Cystathionine in the supernatant was measured by HPLC after derivatization with 0-phthaldialdehyde (OPA) in the presence of b-mercaptoethanol. Twenty ml of the alkylation reaction was injected onto an RP-8 (10 mm particle size, LiChrosorb) column. Buffers used for elution of the OPA fluorescent derivatives were as follows: A, 85 mM sodium acetate and 6% (v/v) acetonitrile (pH 4.5); B, 60% (v/v) acetonitrile. The following linear gradients were used: 40 to 80% B, 0 to 6 min.: 80% B, 6 to 9 min.; 80 to 40% B, 9 to 10 min.; 40% B, 10 to 12 min. (40C, 1 ml/min.). The OPA derivatives were detected by measuring fluorescence at 455 nm after excitation at 340 nm using a Hitachi F-1040 fluorescence detector. Quantitation of cystathionine was carried out by measuring peak areas using the chromatography data analysis software Beckman SYSTEM GOLD. One unit of activity is defined as the formation of 1 mmol of cystathionine per minute.

Amino Acid Analysis

Soluble amino acids from transgenic potato plants were measured by HPLC analysis of tissues extracted with ethanol (Inaba, et al., Plant Physiol. 104:881–887 (1994)) alkylated with phenylisothiocyanate (PITC) (Fierabracci, et al., J. Chromatog. 570(2):285–291 (1991)). Plant samples were ground in liquid nitrogen. Powdered tissue was extracted with 80% (v/v) ethanol. The sample was centrifuged to remove cellular debris. The pellet was re-extracted twice more and the supernatants were pooled. The pooled extracts were loaded on an AG-50W (H+ form, BioRad) column (1.5 ml/mg fresh weight). The column was washed with 6 ml of ethanol followed by 6 ml of water. Amino acids were eluted with 2 ml of 2 M $NH_4OH$. The eluate was dried by evaporation under a stream of $N_2$ gas at 80° C., and the residue dissolved in a solution of 7:1:1:1 (v/v) ethanol-water-triethanolamine-PITC. The PITC derivatives were detected by measuring absorbence at 255 nm. Quantitation of amino acids was carried out by measuring peak areas using Beckman SYSTEM GOLD software. Total amino acid content was calculated as the sum of all peak areas from a chromatograph divided by the fresh weight of the plant sample.

Results

Production of Transgenic Russett Burbank Potato Plants

Russet Burbank potato plants were transformed with *Agrobacterium tumefaciens* carrying the *Arabidopsis* CGS gene under the control of the 35S promoter (CGS+ vector). Ten different transgenic lines were generated. All transgenic lines were phenotypically normal and indistinguishable from the untransformed potato plants. The genomic DNA from the 10 different transgenic lines was digested with KpnI and XbaI to release the 2.0 kb CGS cDNA insert and subjected to Southern blot analysis with $^{32}$P-labeled *Arabidopsis* CGS DNA. The results showed that all transgenic lines contained the 2.0 kb KpnI-XbaI CGS cDNA fragment, indicating that all lines are transformed. The *Arabidopsis* probe did not pick up any signal in the DNA from the wild-type potato plants. Southern blot analysis with genomic DNA digested with KpnI revealed that five transgenic lines are independent transformants. These transgenic lines, CGS1, 2, 4, 8, 10 were chosen for further analysis.

Expression of *Arabidopsis* CGS Gene in Transgenic Potato Plants by Northern Blot Analysis Total RNA was extracted from the leaves and tubers of transgenic potato lines CGS1, 2, 4, 8 and 10 and wild-type potato plants and subjected to Northern blot analysis using $^{32}$P-*Arabidopsis* CGS DNA. The results showed that the *Arabidopsis* CGS gene is expressed in both leaves and tubers of all transgenic potato lines analyzed. CGS1 and CGS8 had the highest levels of *Arabidopsis* CGS transcripts in the leaves and tubers. Expression of *Arabidopsis* CGS gene in transgenic potato plants by Immunoblot analysis.

Immunoblot analysis with *Arabidopsis* CGS-specific antibody demonstrated that the CGS gene is over-expressed in leaves, tubers and roots of the five different transgenic potato lines analyzed. *Arabidopsis* CGS antibody did not crossreact with potato CGS. Thus, we did not observe any signal in the wild-type potato lane, indicating that the high level of expression observed in the transgenic lines is due to expression of the *Arabidopsis* CGS. Although CGS expression levels varied to some extent in the different tissues analyzed, significantly higher levels of *Arabidopsis* CGS were expressed in the tubers of line CGS1. CGS enzymatic activity in transgenic potato lines.

CGS activity was determined in the leaves and roots of transgenic plants and compared to the activity in the leaves and roots of wild-type potato plants. The results shown in Table 1 indicate that CGS enzymatic activity is elevated in the leaves and roots of all transgenic potato lines. Compared with wild-type, five CGS[+] lines, CGS1, 2, 4, 8, and 10 had 2- to 7-fold higher CGS activity in their leaves, with CGS 1 and 8 as the highest. Similarly, CGS activity in the roots of transgenic lines was 2- to 4-fold higher than the CGS activity in the roots of wild-type plants.

TABLE 1

CGS enzyme activity in transgenic potato lines over-expressing CGS

| Line | | Specific activity (nmol·min.$^{-1}$·mg$^{-1}$) |
|---|---|---|
| wild-type potato leaf | | 0.52 ± 0.18 |
| CGS[+] leaf | {CGS1 | 3.48 ± 0.96 |
| | {CGS2 | 1.21 ± 0.88 |
| | {CGS4 | 1.01 ± 0.29 |
| | {CGS8 | 2.74 ± 0.23 |
| | {CGS10 | 1.72 ± 0.63 |
| wild-type potato root | | 0.70 ± 0.11 |
| CGS[+] root | {CGS1 | 2.05 ± 0.17 |
| | {CGS2 | 0.90 ± 0.01 |
| | {CGS4 | 1.78 ± 0.02 |
| | {CGS9 | 2.85 ± 0.14 |
| | {CGS10 | 1.45 ± 0.38 |

CGS enzyme activity was measured in the leaf and root of potato plants. The averages ±SB of two independent experiments are shown.

Methionine Levels in Transgenic Potato Lines

Figure 2:
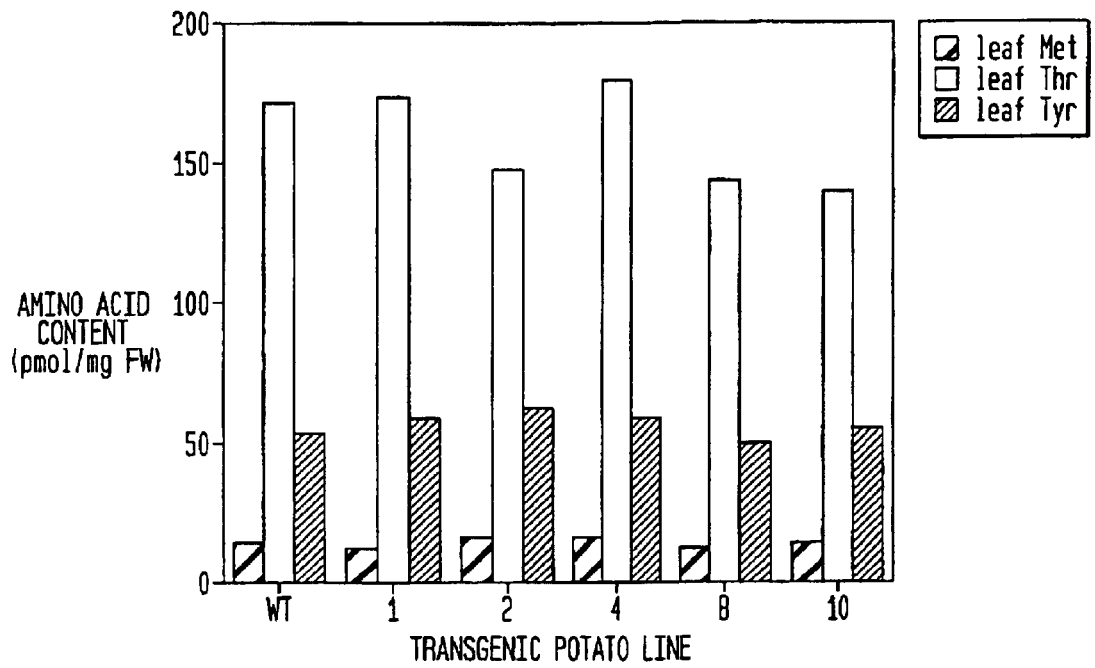
FIG. 2 is a bar graph showing the content (in pmol/mg) of the free amino acids Met, Thr (threonine) and Tyr (tyrosine) in leaves of wild-type and transgenic plants expressing *Arabidopsis* CGS.
Figure 3:
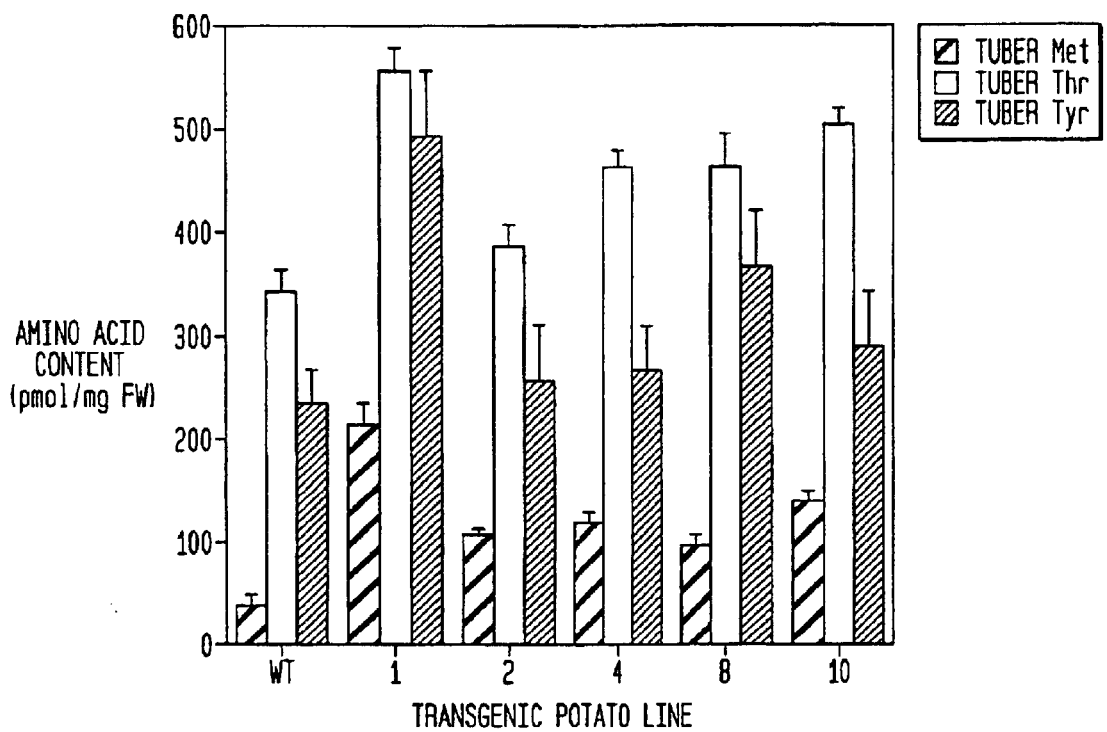
FIG. 3 is a bar graph showing the content (in pmol/mg) of the free amino acids Met, Thr and Tyr in tubers of wild-type and transgenic plants expressing *Arabidopsis* CGS.
Figure 4:
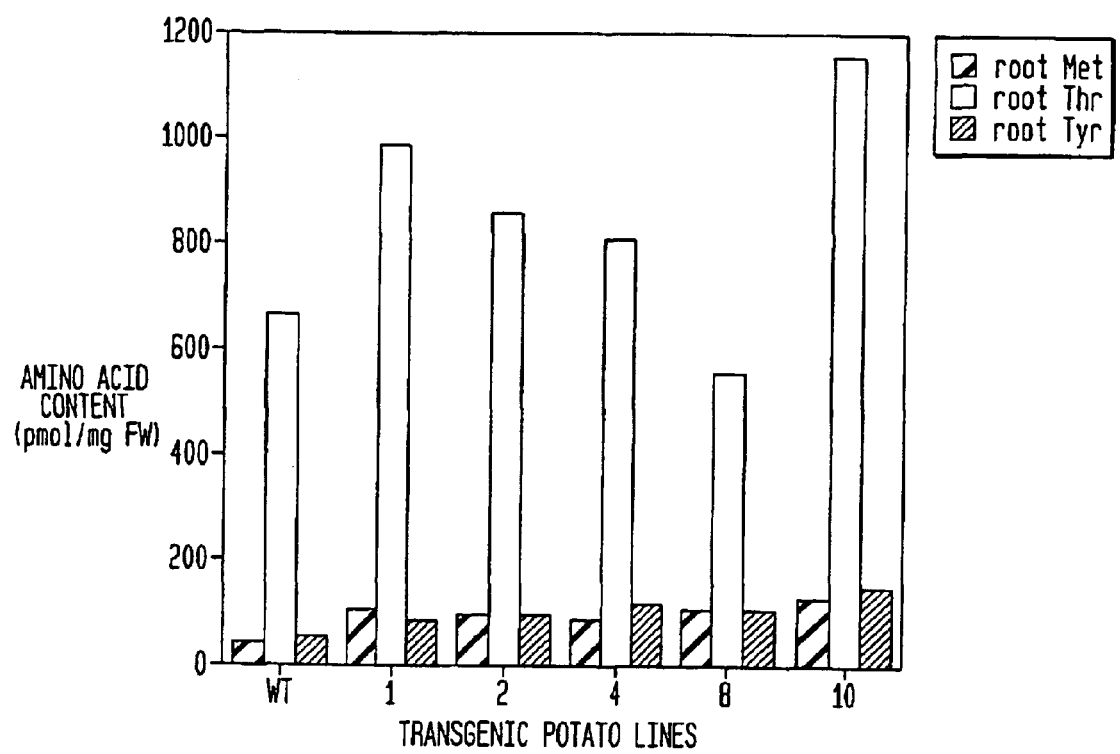
FIG. 4 is a bar graph showing the content (in pmol/mg) of the free amino acids Met, Thr and Tyr in roots of wild-type and transgenic plants expressing *Arabidopsis* CGS.

Free methionine levels in each transgenic potato line was determined by HPLC analysis using ethanol extraction. The results shown in Table 2 and FIG. 2 indicate that the methionine levels in the leaves of transgenic potato plants were similar to the levels in the wild-type plants. Similarly, the levels of other amino acids analyzed, such as Thr and Tyr were similar to the levels in the leaves of wildtype plants. In contrast, as shown in FIG. 3, Met levels in the tubers of transgenic plants were 2- to 5-fold higher than the levels in wild-type tubers, with CGS1 as the highest. Similarly, as shown in FIG. 4, Met levels in the roots of transgenic potato plants were 2- to 2.5-fold higher than the wild-type roots.

TABLE 2

Amino acid content in transgenic potato lines over-expressing CGS

| | | pmol·mg$^{-1}$ FW | | |
|---|---|---|---|---|
| sample | line | Met | Thr | Tyr |
| wild-type leaf | | 21 | 169 | 52 |
| CGS[+]leaf | {CGS1 | 20 | 163 | 56 |
| | {CGS2 | 27 | 154 | 61 |
| | {CG54 | 17 | 167 | 51 |

TABLE 2-continued

Amino acid content in transgenic potato lines over-expressing CGS

| | | pmol·mg$^{-1}$ FW | | |
|---|---|---|---|---|
| sample | line | Met | Thr | Tyr |
| | {CGS8 | 19 | 149 | 44 |
| | {CGS10 | 22 | 139 | 53 |
| wild-type root | | 50 | 659 | 60 |
| CGS[+]root | {CGS1 | 122 | 1001 | 90 |
| | {CGS2 | 101 | 887 | 101 |
| | {CG54 | 91 | 825 | 116 |
| | {CGS8 | 106 | 551 | 105 |
| | {CGS10 | 124 | 1165 | 147 |
| wild-type tuber | | 43 ± 4 | 361 ± 19 | 243 ± 76 |
| CGS[+]tuber | {CGS1 | 212 ± 22 | 544 ± 22 | 485 ± 90 |
| | {CGS2 | 126 ± 12 | 388 ± 63 | 247 ± 52 |
| | {CGS4 | 117 ± 7 | 379 ± 58 | 256 ± 57 |
| | {CGS8 | 109 ± 6 | 453 ± 64 | 378 ± 64 |
| | {CGS10 | 127 ± 30 | 509 ± 67 | 281 ± 99 |

Soluble amino acids were measured in the leaves, roots, and tubers of potato plants. The averages ±SD of three independent experiments are shown. SMM was measured by GC analysis.

Resistance to Ethionine in CGS+ Transgenic Potato Plants

Inaba, et al. used 100 μM ethionine, the toxic analogue of methionine to select *Arabidopsis thaliana* mutants that over-accumulated methionine. We tested the effects of ethionine on the growth of transgenic potato plants by incorporating ethionine into the maintenance medium. Several concentrations of ethionine, 10, 25, 50, 100, 200, 300 μM were tested initially using wild-type potato plants. There was total inhibition of growth at 50 μM and at higher ethionine levels. When transgenic potato plants were tested on 25 and 50 μM ethionine, only CGS4 and CGS8 had limited growth of roots. However, at 10 μM ethionine, all transgenic plants initiated roots in three days. The transgenic plants continued to grow while the growth of wild-type plants were inhibited. These results demonstrate the use of ethionine as a selection agent to identify CGS over-expressors.

Discussion

The loss of the flavor compound methional during processing is a significant problem for the food processing industry. We present evidence that by introducing the *Arabidopsis* CGS cDNA, encoding the rate limiting enzyme in methionine biosynthesis, we were able to enhance the production of methionine, the precursor for methional, in the tubers of transgenic potato plants. Expression of the homologous CGS gene in transgenic plants, either did not result in increases in Met production in the leaves or led to co-suppression, resulting in abnormal plants. There is approximately 75% homology between the *Arabidopsis* and potato CGS genes. This level of homology was not sufficient to give a cross-reaction when DNA probes or the antibodies were used. Gene silencing or co-suppression may not have occurred in our transgenic potato plants expressing the heterologous *Arabidopsis* CGS gene because the two genes are not closely related. Hence, all transgenic lines had increased CGS expression.

Analysis of the amino acid content in five CGS[+] potato lines revealed that the Met levels in the leaves are similar to the levels in wild-type plants. Although the CGS protein and activity were elevated in the leaves, corresponding increases in Met levels were not observed. In contrast, by comparison to wild-type plants, the tubers and roots of the transgenic potato lines showed 2- to 7-fold higher Met levels. The lack of increase in Met levels in the leaves could be because Met is not stable in the leaves or alternatively Met could be transported from the leaves into the sink organs in potato. Similar results were observed with the *Arabidopsis* mutant mtol that overaccumulates soluble Met. Inaba, et al., (1994) reported that mtol over-accumulates Met 10- to 40-fold more than the wild-type in aerial parts during the vegetative growth period. However, when the mutant plants start to flower, the soluble Met leaves in the vegetative tissues drop to the level in the wild type, while Met levels in the inflorescence and immature fruits increase to 5- to 8-fold higher levels than the wild-type. These results, together with our results in transgenic plants suggest that soluble Met is translocated to sink organs after the onset of reproductive growth.

Example 2

Modulation of SAM Synthetase Expression in *Arabidopsis* Affects CGS Expression and Met Production The preparation of transgenic *Arabidopsis* (Columbia) transformed with pO35SSAM (SAMS[+] construct) has been previously described (de Carvalho, et al., "Post-transcriptional gene silencing in transgenic plants," in *Plant Molecular Biology: Molecular Genetic Analysis of plant development and metabolism*, (NATO-ASI Series H, Vol. 81), Coruzzi et al., eds., Berlin, Springer Verlag (1994) on pages 437–452)). SAMS[+] plants were raised in a 23° C. growth chamber with a light intensity of ~100 $\mu$E/m/s and a photoperiod of 14 hr. light followed 10 hr. of darkness.

SAMS suppression profoundly effects development in *Arabidopsis*. Plant lines derived from transformation with the SAMS[+] construct produced progeny with widely differing morphologies resulting from co-suppression of SAMS classified MUT1, MUT2, and MUT3 by severity of phenotypes.

The plants with normal morphology, termed MUT1, over-expressed SAMS. Stunted plants, termed MUT2 and MUT3, resulted from silencing of the transgene and endogenous gene (de Carvalho, et al., supra). All the plants appeared normal during the early stages of growth but as they grew the morphological types appeared when a switch to the co-suppressed state occurs, and this state persisted throughout further development (de Carvalho, et al., supra). MUT3 became co-suppressed the earliest while MUT2 became co-suppressed late. The morphological abnormalities of MUT3 plants were strikingly similar to those of CGS[−] plants (photographs not shown) in that numerous apical shoots were produced that failed to develop fully and the oldest leaves become thickened and curled (photograph not shown). Another similarity is that MUT3 plants were unable to flower. Although MUT2 plants were able to flower, the inflorescences were stunted and distorted (photographs not shown). SAMS suppressed plants differ from CGS[−] (photographs not shown) in that Met feeding had no effect on the ability of MUT3 to flower as it did on the CGS[−] plants. Although the frequencies with which the SAMS plant-types were produced is unpredictable, drought or antibiotic stress during the early growth period were noted to promote the formation of MUT2 and MUT3 and decrease the frequency with which the MUT1 type was produced.

Immunoblot analysis confirmed that SAMS protein was overproduced in the MUT1 type and was decreased in the MUT2 and MUT3 types (photographs not shown). The levels of SAMS protein in the leaves of the sense and co-suppressed SAMS transformants were determined by immunoblot with antibody against *C. roseus* SAMS. A broad range of SAMS expression levels was shown in the leaves of both the sense and co-suppressed SAMS transformants (photographs not shown). SAMS protein levels in leaves of two MUT1 morphological types transformed with the SAMS[+] construct were several fold higher than wild-type. In case of the co-suppressed transgenic plants in MUT2 and MUT3 types, several fold lower SAMS levels than wild type were detected (photographs not shown). Enzyme assay of leaf extracts from the transgenic plants, MUT1 and MUT3, showed that SAMS enzyme activity also correlated with the immunoblot results (results not shown).

In the simultaneous immunoblot analysis for SAMS and CGS protein level, MUT2 and MUT3 plant leaves showed decreased SAMS levels (as expected due to co-suppression) but the reverse pattern of expression was observed for CGS. The CGS enzyme was over-produced in MUT2 and MUT3 and was slightly lower in MUT1 (photographs not shown). In case of SAMS co-suppression, it is expected that tissue level of SAM is decreased because of blockage of its synthesis. CGS was induced in case of SAMS co-suppression with expected lower SAM.

Measurement of enzyme activity confirmed the immunoblot results in that CGS activity in MUT3 plants was 0.91±0.03 nmol.min$^{-1}$.mg protein$^{-1}$, corresponding to an increase of approximately 3 fold compared with wild-type plants.

Amino acid analysis revealed that MUT2 and MUT3 plants greatly accumulated free Met ~160 and ~210 fold, and SMM ~100 and ~150 fold, respectively, above the level in wild-type; while MUT1 contained approximately the same level as wild-type. Thr was also increased in MUT2 and MUT3, paralleling a 3 to 5 fold increase of all amino acids. In addition to the interpretation from the amino acid analysis in CGS[−] plants, the development of abnormality in SAMS co-suppression might be correlated with the increase in total amino acids. These findings indicate that the increase of CGS expression in MUT2 and MUT3 plants is due to a deficiency of SAM rather than Met.

Discussion

With the transgenic plants cosuppressing and overexpressing SAMS in *Arabidopsis* (de Carvalho et al., supra, 1994) it became possible to investigate the exact regulator and the possible mechanisms for regulation in Met biosynthesis. Met feeding in wild-type plants is shown to inhibit CGS expression. It suggests that Met or a Met metabolite control the gene expression of CGS. The analysis of plants having SAMS co-suppression show endogenous accumulation of Met along with induction of CGS expression. The immunoblotting for CGS and SAMS expression using SAMS co-suppressed plants revealed that in case of SAMS expression is suppressed which assumes consequently decreased SAM level, CGS is induced. Those results implicate that SAM rather than Met is the regulator t molecule for regulation of CGS expression.

These findings also implicate that SAM rather than Met is placed the final product of the pathway and is responsible for regulation of its synthesis. This means the pathway would call SAM biosynthetic pathway rather then Met biosynthesis. In total, an hypothesis in the overall view of the regulation in Met synthesis is proposed that SAM down-regulates the gene expression of CGS as well as allosteric activation of TS in regulation of Met biosynthesis in plants (photographs not shown).

INDUSTRIAL APPLICABILITY

The present invention pertains to the field of agricultural biotechnology and food science, and entails the production of transgenic plants that when processed into various food products, possess enhanced flavor quality and/or stability. It also pertains to methods for selecting transformed plant cells using a specific selection agent and marker gene combination. The method is useful in selecting plant cells that express a nucleic acid of interest versus plant cells that do not express the nucleic acid of interest.

Modifications of the presently disclosed modes of carrying out the invention that are obvious to those skilled in the fields of agricultural biotechnology, biochemistry, food science and related arts are intended to be within the scope of the following claims.

All patent and non-patent publications cited in this specification are indicative of the level of skill of those skilled in the art to which this invention pertains. All these publications and patent applications are herein incorporated by reference to the same extent as if each individual publication or patent application was specifically and individually indicated to be incorporated herein by reference.

What is claimed is:

1. A method of selecting plant cells that contain a non-native nucleic acid of interest, comprising transforming plant cells with a first chimeric nucleic acid containing in operable association a first promoter functional in a plant cell and a first DNA molecule of interest, and a second chimeric nucleic acid containing in operable association a second promoter and a second DNA molecule encoding a cystathionine gamma synthase that permits the selection of transformed plant cells transformed with said chimeric nucleic acid molecules by rendering said transformed plant cells resistant to an amount of ethionine that would be toxic to plant cells that do not express said second DNA molecule; culturing the plant cells in medium containing ethionine in an amount that would be toxic to plant cells that do not express said second DNA molecule; and selecting plant cells that grow in said medium.

2. A composition of matter, comprising (a) plant cells transformed with a first chimeric nucleic acid comprising in operable association a first promoter functional in a plant cell and a first DNA molecule of interest, and a second chimeric nucleic acid comprising in operable association a second. promoter functional in the plant cell and a second DNA molecule encoding a cystathionine gamma synthase, and (b) ethionine in. an amount that would be toxic to plant cells that do not express a DNA molecule encoding a cystathionine gamma synthase.

3. The method of claim 1, wherein the plant cells are monocot cells.

4. The method of claim 1, wherein the plant cells are dicot cells.

5. The method of claim 4, wherein the dicot plant cells are potato cells.

6. The composition of claim 2, wherein the plant cells are monocot cells.

7. The composition of claim 2, wherein the plant cells are dicot cells.

8. The composition of claim 7, wherein the dicot plant cells are potato cells.

* * * * *

UNITED STATES PATENT AND TRADEMARK OFFICE
CERTIFICATE OF CORRECTION

PATENT NO. : 6,821,781 B1
DATED : November 23, 2004
INVENTOR(S) : Nilgun E. Tumer and Thomas Leustek It is certified that error appears in the above-identified patent and that said Letters Patent is hereby corrected as shown below:

Column 2,
Line 2, after "increase" delete "to".

Column 3,
Line 34, after "Plant" delete "is".
Line 35, after "transformed" delete "a".

Column 10,
Line 66, after "tubers", end paragraph.
Line 66, "Expression" should start a new paragraph.

Column 11,
Line 42, in Table 1, "±SB" should read -- ±SE --.

Column 14,
Line 53, after "regulator", delete "t".

Column 15,
Line 29, delete the first occurrence of "transformed".

Column 16,
Line 12, after "second", delete ".".
Line 14, after "in", delete ".".

Signed and Sealed this

Nineteenth Day of April, 2005

JON W. DUDAS
*Director of the United States Patent and Trademark Office*